US00PP11510P

United States Patent [19]

Hubbard et al.

[11] Patent Number: Plant 11,510

[45] Date of Patent: Sep. 12, 2000

[54] PHOTINIA PLANT NAMED 'COLANGO'

[75] Inventors: Agnes Hubbard, Fair Oaks; James Spivey, Devine, both of Tex.

[73] Assignee: Color Spot Nurseries, Inc., Pleasant Hill, Calif.

[21] Appl. No.: 09/129,435

[22] Filed: Aug. 5, 1998

[51] Int. Cl.[7] ..... A01H 5/00

[52] U.S. Cl. ..... Plt./226

[58] Field of Search ..... Plt./226

[56] References Cited

U.S. PATENT DOCUMENTS

P.P. 5,237 5/1984 Espinosa ..... Plt./226

*Primary Examiner*—Howard J. Locker
*Assistant Examiner*—Wendy A Baker
*Attorney, Agent, or Firm*—C. A. Whealy

[57] ABSTRACT

A new and distinct cultivar of Photinia plant named 'Colango', characterized by its upright and somewhat outwardly spreading plant form; vigorous and freely branching plant habit; short internodes; sharply serrated leaf margins; shiny dark red young foliage; undulating dark green mature foliage; and long-lasting red leaf color.

1 Drawing Sheet

BACKGROUND OF THE INVENTION

The present invention relates to a new and distinct cultivar of Photinia, botanically known as *Photinia×fraseri*, and hereinafter referred to by the cultivar name Colango.

The new Photinia is a product of a planned breeding program conducted by the Inventors in San Antonio, Tex. The objective of the breeding program was to create new Photinias with darker leaf color, longer-lasting red leaf color, better vigor, and better tolerance to high temperatures. The new Photinia originated from a self-pollination of the commercial *Photinia×fraseri* cultivar Birmingham (not patented).

The cultivar Colango was discovered and selected by the Inventors as a single plant within a population of 8,000 progeny plants in a controlled environment in San Antonio, Tex., in July, 1995. The selection of this plant was based on its desirable plant form, leaf shape and unique foliage coloration.

Asexual reproduction of the new Photinia by terminal cuttings taken in a controlled environment in San Antonio, Tex., has shown that the unique features of this new Photinia are stable and reproduced true to type in successive generations.

BRIEF SUMMARY OF THE INVENTION

Plants of the new Photinia have not been observed under all possible environmental conditions. The phenotype may vary somewhat with variations in environment such as temperature, daylength, light intensity, nutrition and water status without, however, any variance in genotype.

The following traits have been repeatedly observed and are determined to be the unique characteristics of 'Colango'. These characteristics in combination distinguish 'Colango' as a new and distinct cultivar:

1. Upright and somewhat outwardly spreading plant form.

2. Vigorous, dense and bushy plants that are freely branching with short internodes.

3. Sharply serrated dark red young foliage and undulating dark green mature foliage.

4. Long-lasting red leaf color.

Compared to plants of the Photinia cultivar Colmont, disclosed in U.S. Plant Pat. application Ser. No. 09/129,441, plants of the new Photinia are shorter, less upright and more outwardly spreading, more vigorous and have broader leaves.

In side-by-side comparisons conducted by the Inventors in San Antonio, Tex., plants of the new Photinia differ from plants of the parent cultivar, Birmingham, and plants of the commercial *Photinia×fraseri* cultivar Red Robin in the following characteristics:

1. Plants of the new Photinia are more upright than plants of the cultivars Birmingham and Red Robin.

2. Plants of the new Photinia are more freely branching after pruning than plants of the cultivars Birmingham and Red Robin.

3. Plants of the new Photinia have shorter internodes than plants of the cultivars Birmingham and Red Robin.

4. Plants of the new Photinia have darker-colored foliage than plants of the cultivars Birmingham and Red Robin.

5. Plants of the new Photinia have longer-lasting red foliage color than plants of the cultivars Birmingham and Red Robin.

A detailed comparison of the cultivars Colango, Birmingham and Red Robin appears in Chart A at the end of the specification.

BRIEF DESCRIPTION OF THE PHOTOGRAPH

The accompanying colored photograph illustrates the overall appearance of the new Photinia, showing the colors as true as it is reasonably possible to obtain in colored reproductions of this type. The photograph comprises a side perspective view of a typical containerized plant of 'Colango'. Foliage colors in the photograph may appear different from the actual colors due to light reflectance.

DETAILED BOTANICAL DESCRIPTION

The following observations, measurements, values, and comparisons describe plants grown in San Antonio and Keller, Tex., under outdoor conditions which closely approximate commercial production conditions. Plants used for the description were grown in 25-cm containers and were approximately one year old.

In the following description, color references are made to The Royal Horticultural Society Colour Chart except where general terms of ordinary dictionary significance are used.

Botanical classification: *Photinia×fraseri* cultivar Colango.

Parentage: Self-pollination of *Photinia×fraseri* cultivar Birmingham.

Propagation:

*Type.*—By terminal cuttings.

*Time to initiate roots.*—Summer: About 56 to 70 days at temperatures of 29 to 35° C. Winter: About 84 to 112 days at temperatures of 22° C.

*Time to develop roots.*—Summer: About 100 to 120 days at temperatures of 29 to 35° C. Winter: About 134 to 160 days at temperatures of 22° C.

*Rooting habit.*—Numerous, fibrous.

Plant description:

*Plant form and growth habit.*—Perennial evergreen shrub, upright and somewhat outwardly spreading, uniform and dense plant habit. Vigorous.

*Branching habit.*—Responds well to pruning; freely branching, typically about five lateral branches develop after removal of terminal apex.

*Plant height.*—About 68 cm.

*Plant diameter.*—About 70 cm.

*Lateral branch description.*—Diameter: About 1.3 cm. Internode length: Closely spaced; about 1.5 cm. Color: Woody: Gray, close to 197A. Young: Close to 187A. Texture: Woody stems with lenticels; young stems, smooth. Lenticels: Oval in shape; less than 1 mm in length; dense; gray, close to 197A, in color.

Foliage description:

*Arrangement.*—Alternate, single.

*Length.*—About 8.9 cm.

*Width.*—About 4.1 cm.

*Shape.*—Oblong to obovate.

*Apex.*—Acute or rounded.

*Base.*—Attenuate.

*Margin.*—Sharply serrated.

*Texture.*—Leathery, tough, very durable; glabrous, somewhat glossy.

*Aspect.*—Undulate.

*Color.*—Young foliage, upper surface: Shiny; 183A to darker than 187A to 200C with dark red, 187A, tones. Young foliage, lower surface: 183B to 183C to 187A. Mature foliage, upper surface: Dark green, much darker than 147A to 139A. Mature foliage, lower surface: 182B to close to 144A.

*Petiole.*—Length: About 1.1 cm. Diameter: About 2 mm. Color: Close to 146A with dark red, close to 187A, tones.

Flower description: Flowers insignificant and typical of species.

*Natural flowering season.*—Early spring.

*Flower arrangement.*—Flowers arranged in terminal corymbose panicles.

*Flower appearance.*—Single flowers, perfect; petals white to creamy white.

Disease resistance: No known Photinia diseases observed to date on plants grown under commercial greenhouse conditions. Plants of the new Photinia appear to be more tolerant to leaf spot-causing pathogens common to Photinias.

Seed production: Seed production has not been observed.

CHART A

| CHARACTERISTIC | 'COLANGO' | 'BIRMINGHAM' | 'RED ROBIN' |
|---|---|---|---|
| GROWTH HABIT, PLANT SHAPE | Upright, somewhat outwardly spreading | Outwardly spreading | Upright and outwardly spreading; open form |
| NUMBER OF LATERAL BRANCHES FORMED AFTER PRUNING | About 5 | About 4 | About 4 |
| INTERNODE LENGTH | About 1.5 cm | About 2.25 cm | About 3 cm |
| LEAF ASPECT | Undulate | Concave | Concave |
| LEAF MARGIN | Sharply serrate | Serrate | Serrate |
| LEAF COLOR, YOUNG, UPPER SURFACE | 183A to darker than 187A to 200C with dark red, (87A) tones | 185A | 178A |
| LEAF COLOR, YOUNG, LOWER SURFACE | 183B to 183C to 187A | 184A/184B | 178B |
| LEAF COLOR, MATURE, UPPER SURFACE | Much darker than 147A to 139A | 139A | 137A |
| LEAF COLOR, MATURE, LOWER SURFACE | 182B to close to 144A | 146B/146C | 146B/146C |

It is claimed:

1. A new and distinct Photinia plant named 'Colango', as illustrated and described.

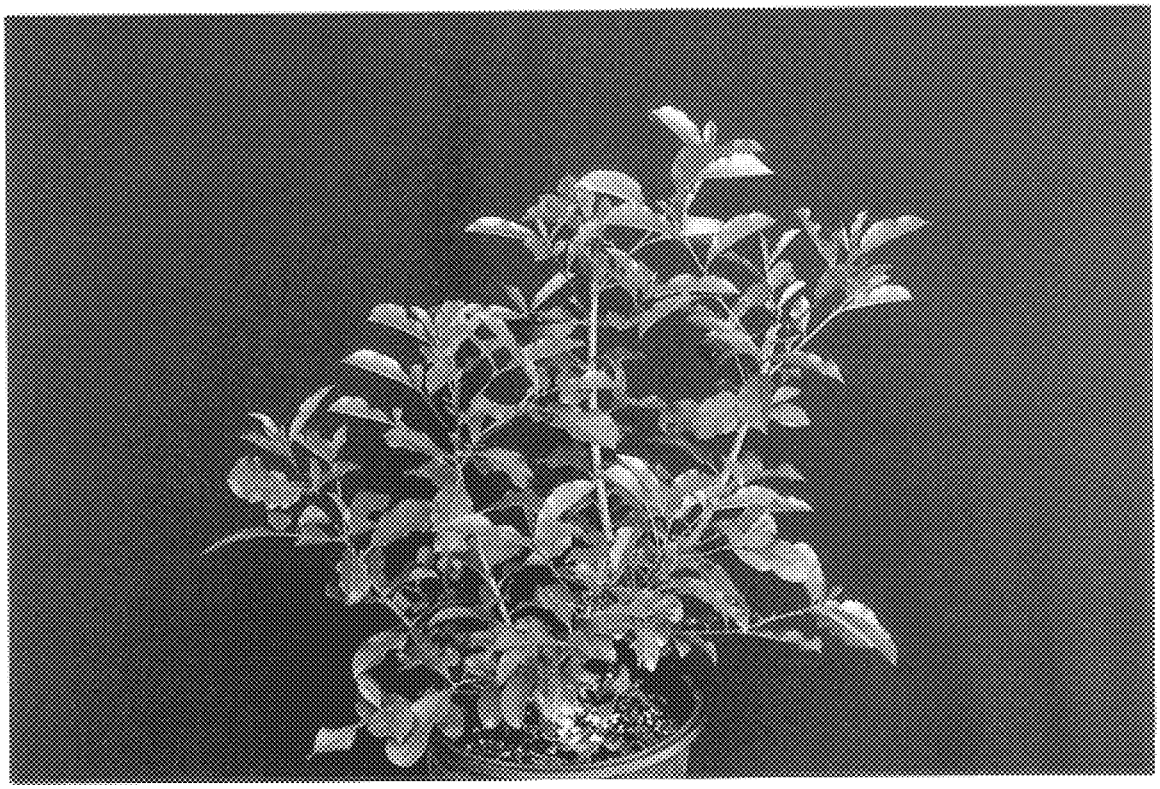

* * * * *